(12) United States Patent
Grisenti et al.

(10) Patent No.: US 7,667,056 B2
(45) Date of Patent: Feb. 23, 2010

(54) PROCESS AND NEW INTERMEDIATES FOR THE PREPARATION OF STEROIDS WITH A PROGESTOGEN ACTIVITY

(75) Inventors: Paride Grisenti, Milan (IT); Fabio Pecora, Milan (IT); Elisa Verza, Milan (IT); Massimo Leoni, Milan (IT); Laura Bossi, Milan (IT)

(73) Assignee: Poli Industria Chimica S.p.A. (IT)

( * ) Notice: Subject to any disclaimer, the term of this patent is extended or adjusted under 35 U.S.C. 154(b) by 908 days.

(21) Appl. No.: 10/523,058

(22) PCT Filed: Jul. 31, 2003

(86) PCT No.: PCT/EP03/08505

§ 371 (c)(1), (2), (4) Date: Feb. 2, 2005

(87) PCT Pub. No.: WO2004/014934

PCT Pub. Date: Feb. 19, 2004

(65) Prior Publication Data

US 2005/0234251 A1    Oct. 20, 2005

(30) Foreign Application Priority Data

Aug. 2, 2002    (IT) .......................... MI2002A1755

(51) Int. Cl.
C07J 1/00    (2006.01)
C07J 21/00    (2006.01)

(52) U.S. Cl. ...................... 552/526; 552/648; 552/650; 540/33

(58) Field of Classification Search .................. 540/33; 552/526, 648, 650
See application file for complete search history.

(56) References Cited

U.S. PATENT DOCUMENTS

| | | | |
|---|---|---|---|
| 3,395,080 A | | 7/1968 | Greenspan et al. |
| 3,927,046 A | * | 12/1975 | van den Broek ............. 552/511 |
| 5,140,106 A | | 8/1992 | Winterfeldt et al. |
| 5,831,104 A | * | 11/1998 | Ring et al. .................. 552/619 |
| 6,395,901 B1 | | 5/2002 | Mangia et al. |

FOREIGN PATENT DOCUMENTS

| | | |
|---|---|---|
| DE | 2361120 A1 | 6/1974 |
| EP | 0114984 A2 | 8/1984 |
| GB | 1128044 A | 9/1968 |

OTHER PUBLICATIONS

Schwarz et al., "Synthesis of 13-Ethyl-11-methylene-18, 19-dinor-17-alpha-pregn-4-en-20-yn-17-ol (Desogestrel) and its Main Metabolite 3-Oxo-Desogestrel." Tetrahedron, vol. 5, No. 36, 1994, pp. 10709-10720, XP000611446 pp. 10711-10713, schemes 4-6.

Gao et al., "Synthesis of 13-ethyl-17-hydroxy-11-methylene-18, 19-din-or-17alpha-pregn-4-en-20-yn-3-one (3-oxo desogestrel)." Steroids, vol. 62, 1997, pp. 399-402, XP004082728, p. 401, scheme 4.

Gribble, G.W. et al., "Reactions of Sodium Borohydride in Acidic Media; VII. Reduction of Diaryl Ketones in Trifluoroacetic Acid," Synthesis, vol. 10 (1978), pp. 763-765.

Smith, H., et al., "Totally Synthetic(+-)-13-Alkyl-3-hydroxy and Methoxy-gona-1,3,5(10)-trien-17-ones and Related Compounds," Experentia, 19, (1963), pp. 394-396.

Green, T., "Protective Groups in Organic Synthesis, 3rd Edition, (1999) p. 297.

* cited by examiner

Primary Examiner—Barbara P Badio
(74) Attorney, Agent, or Firm—Fredrikson & Byron, PA

(57) ABSTRACT

The present invention relates to a new process of synthesis and to some new intermediates for the preparation of steroids with progestogen activity, more particularly, for the preparation of Desogestrel of formula (I). Said process is characterized by the regioselective reduction of the compound of formula (II) to give the intermediate of formula (III).

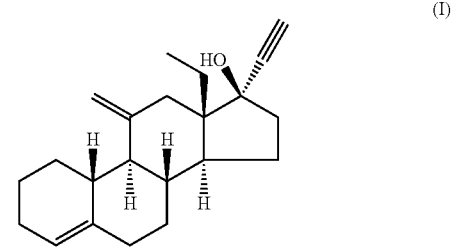

(I)

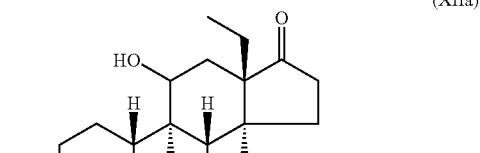

(XIIa)

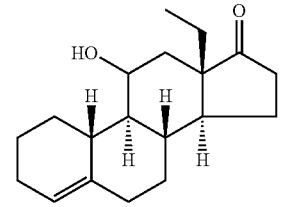

(XIVa)

30 Claims, No Drawings

PROCESS AND NEW INTERMEDIATES FOR THE PREPARATION OF STEROIDS WITH A PROGESTOGEN ACTIVITY

RELATED APPLICATIONS

This application is a 35 U.S.C. 371 national stage filing from International Application No. PCT/EP2003/008505 filed Jul. 31, 2003 and to Italian Application No. MI2002A001744 filed Aug. 2, 2002, the teachings of which are incorporated herein by reference.

The present invention relates to a new process and to new intermediates for preparing compounds with progestogen activity and, more particularly, a process for preparing Desogestrel.

Some synthetic steroidal compounds with progestogen activity such as Desogestrel, Gestodene, Etonogestrel and Levogestrel (FIG. 1) have been used in therapy as contraceptives, either alone or associated with estrogens.

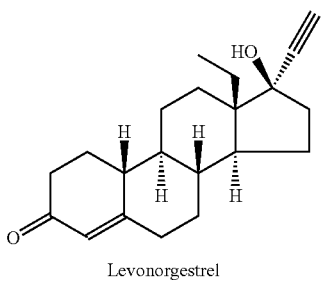

Levonorgestrel

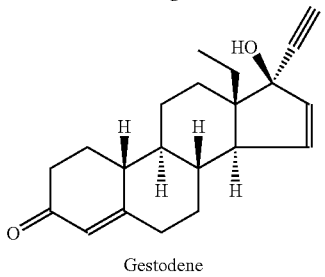

Gestodene

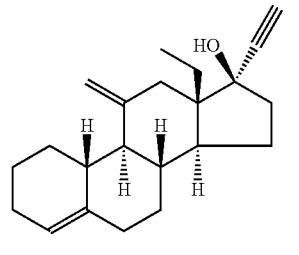

Desogestrel

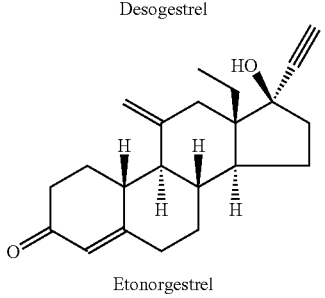

Etonorgestrel

FIG. 1. Progestogens of Second and Third Generation

The above mentioned molecules represents the last development of synthetic progestogens, which can minimize the side effects usually associated with the therapeutic use of such compounds. These unwanted side effects, especially related to the therapeutical use of progestogens of the first generation (FIG. 2), are mainly represented by an increased risk of cardiovascular diseases and by some hepatic disorders.

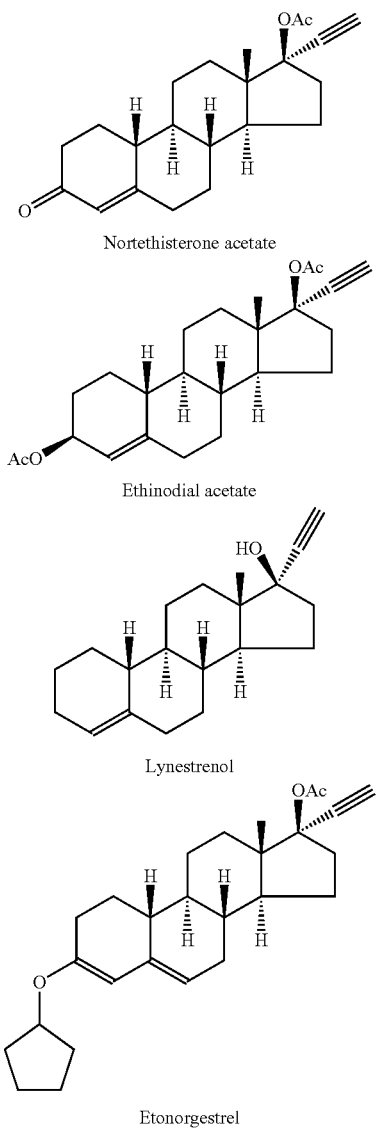

Nortethisterone acetate

Ethinodial acetate

Lynestrenol

Etonorgestrel

FIG. 2. Progestogens of First Generation

A common structural feature of the second and third generation progestogens is represented by the presence of an ethyl group at the 13 beta position and at the 17 position a beta hydroxyl and alfa ethinyl; Desogestrel represents among these derivatives one of the most used in therapy.

The synthesis of Desogestrel was described, for the first time, in the German patent DE 2.361.120.

They key steps of the synthesis of Desogestrel (scheme 1), described in the above mentioned patent, are the oxidation of the 18 methyl group of the compound of formula m, after protection of the carbonyl groups, to give the lactone of formula IV, the conversion of said lactone into the 13-ethyl steroid of formula V, by a Grignard reaction and Wolff-Kishner reduction, the subsequent oxidation of the hydroxy group at the 11 position into a ketone and the Wittig reaction to furnish the 11-methylene derivative, its deprotection at the 3 and 17 positions to give the dione of formula VI which, by a selective thioacetylization, ethinylation at 17 and reduction of the 3 thioacetal, lead to Desogestrel.

Scheme 1

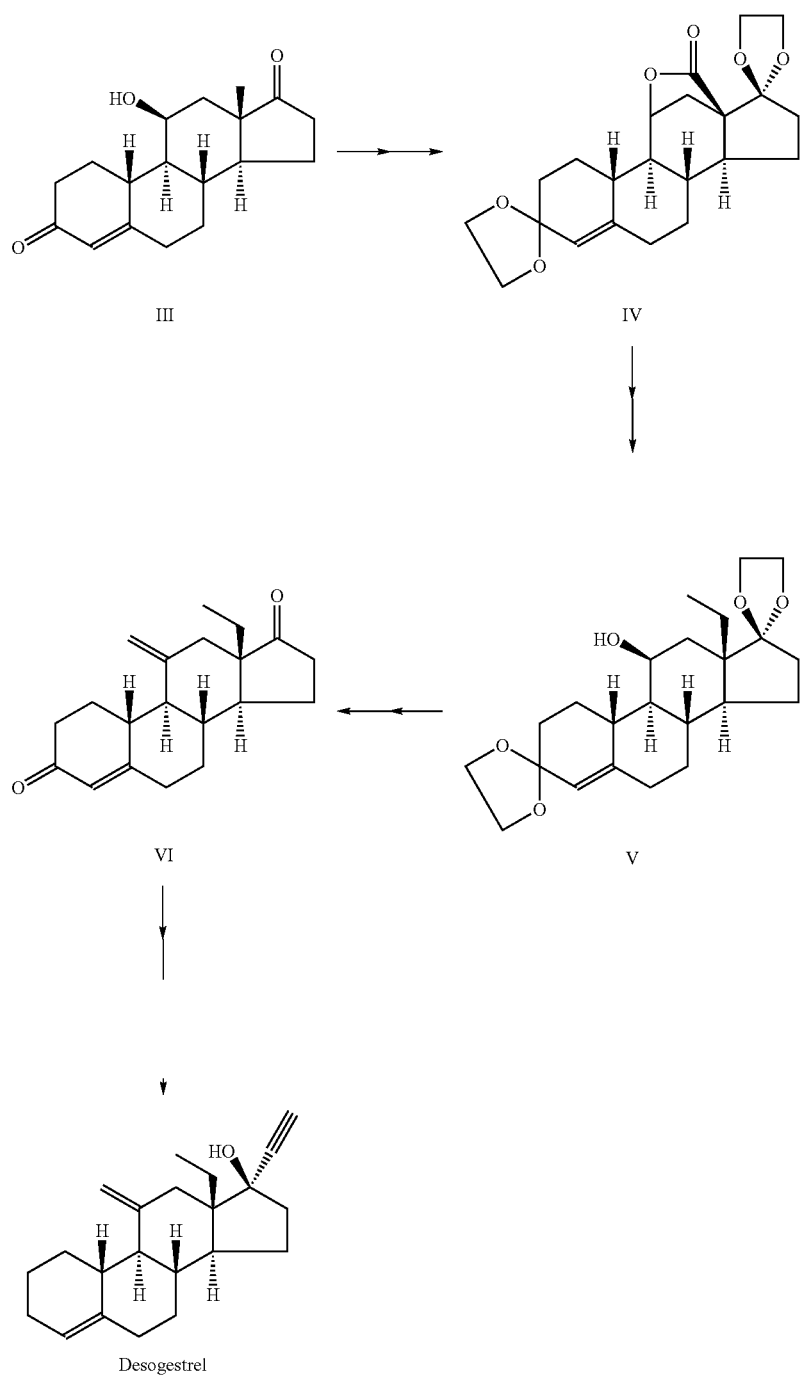

This synthetic route is, from a preparative point of view, very troublesome with reference to both the number of steps required and the danger of some reagents used, such as, for example, lead tetraacetate, methylmagnesium bromide and hydrazine.

The U.S. Pat. No. 5,831,104 (Jenapharm GmbH), describes a different synthetic approach for Desogestrel (scheme 2) which starting from the compound of formula VII by reduction of the carbonyl at 3 with cerium chloride/sodium borohydride, methylation of the so formed hydroxyl and its subsequent reduction leads to the compound of formula VIII which, by oxidation of the hydroxy moieties at 11 and 17 provides the diketones of formula IX.

Finally, by selective protection of the ketone at 17 as ketal which affords the compound of formula X, Wittig reaction on the ketone at the 11 position and ethinylation at 17, Desogestrel is obtained.

Scheme 2

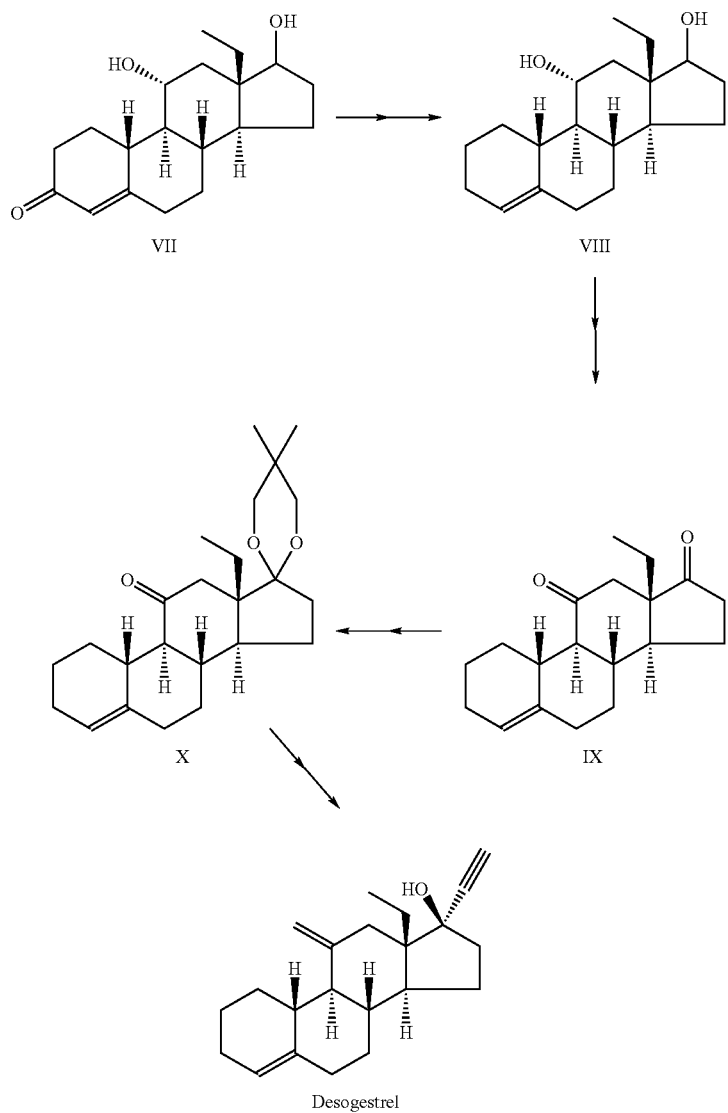

This second synthetic approach is advantageous in that the starting compound of formula VII, obtainable by total synthesis as described for example in the patent GB 1,128,044, is commercially available.

However, the practical realization of what described in the U.S. Pat. No. 5,831,104 gives Desogestrel with very low total reaction yields: the ketalization process which should selectively lead to the compound of formula X is, in fact, particularly critical. On this purpose, we have verified that the raw product resulting from ketalization is practically made of a mixture of mono and diketal and that the desired intermediate X must be necessarily purified before going on with the subsequent synthetic steps.

We have now developed a new process for preparing Desogestrel that allows to obtain higher yields through new synthetic intermediates, easily purifyable from reaction by-products.

In addition, the new process allows for using a commercial starting material thus limiting the use of disadvantageous reagents and dangerous reaction conditions.

The compound of formula

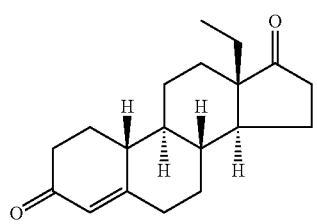

XI (13-ethyl-gon-4-en-3,17-dione, RN 21800-83-9), commercially available, is particularly interesting for performing the process object of the present invention in that it has, inter alia, the ethyl group already inserted at the 13 position.

It may optionally be prepared, as a racemate, as described by H. Smith et al., in Experienta, 19, 394, (1963) and in optically active form (form d) as reported in U.S. Pat. No. 3,395,080.

The synthetic steps, needed for providing Desogestrel starting from this substrate, include:
functionalyzing the 11 position
eliminating the carbonyl function which is present at the 3 position.

The introduction of the hydroxy group at the 11 position is performed by microbiological transformation:

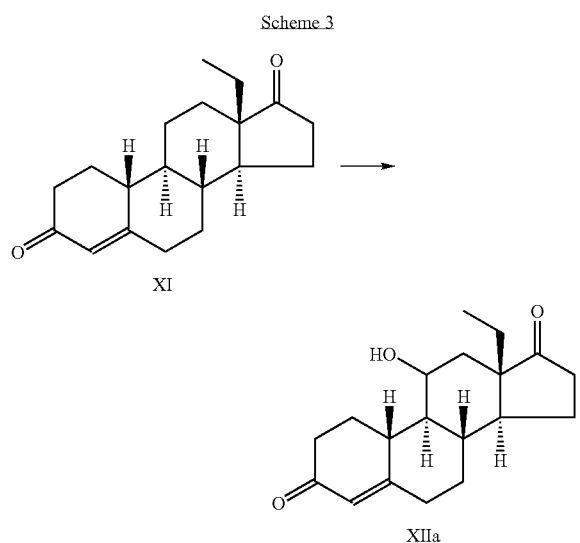

as described in the patent EP0114984.

In particular, after hydroxylation with *Aspergillus ochraceous*, it is possible to isolate, with yields generally varying from 35 to 60%, the corresponding product XIIa, hydroxylated at the 11 position.

This microbiological hydroxylation may be performed with a substrate concentration generally between 2 and 6 g/l of biomass, preferably 5 g/l, with a biotransformation time usually of between 20 and 32 hours.

On the so obtained compound XII is then performed the conversion of the 3 keto group into the corresponding $CH_2$ hydrocarbon function.

Several classical reactions of reduction of carbonyl groups are known in the art, such as the Clemmensen reaction, the Wolff-Kishner reaction or the reduction of thioketals that, as known, provide for the use of very toxic (hydrazine, mercury), dangerous reagents (nickel Raney) and extreme experimental conditions (such as, for example, the temperatures required for the reduction of the intermediate hydrazone in the Clemmensen reduction: 150-200° C.).

These reactions have been discharged for the above mentioned reasons, in that hardly practicable on an industrial scale and with a great environmental impact because of the toxicity of the produced waste.

It is known, from the literature, that borohydrides and, in particular, sodium borohydride, are the most handy, from the safety point of view, among the commercially available reducing agents; said reducing agents, which used as such can reduce the carbonyl groups to the corresponding alcohol groups, under determined experimental conditions and by adding particular salts, form mixed hydrides with an increased reducing power, which can reduce functional groups such as amides to amines or ketone compounds to the corresponding hydrocarbon function (U.S. Pat. No. 6,395,901 B1; Gribble et al. Synthesis, vol. 10, pp 763-765, 1978).

Based on what described in the literature, however, it was foreseeable that by applying the above mentioned experimental conditions to the compound of formula XIIa, it should have happened the simultaneously reduction of both the carbonyls at the 3 and 17 positions, to give the compound of formula XIII according to the following scheme:

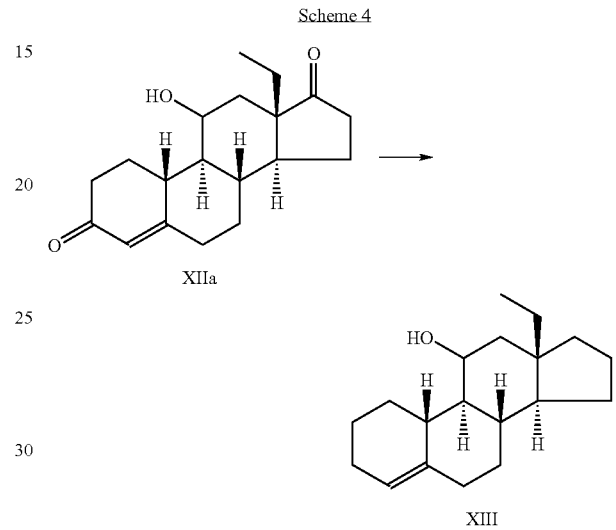

Surprisingly, under the herein adopted experimental conditions, a regioselectivity not supported by any literature data was observed, thus allowing to isolate the compound of formula XIVa with high yields. In this reaction (a), in fact, only the ketone group present at the 3 position results transformed into the corresponding hydrocarbon ($CH_2$), without having the simultaneous reduction of the ketone at 17, as herein disclosed:

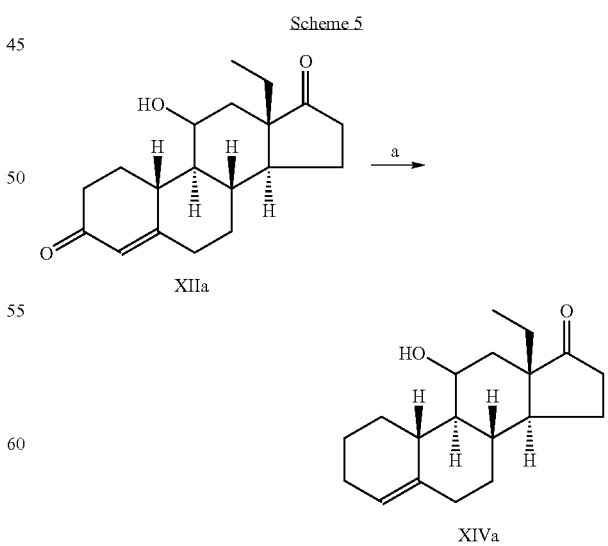

The compound of formula XIV is new and represents a further object of the present invention. It represent a precious intermediate for the preparation of Desogestrel in that it is characterized by the presence of different functional groups at the 11 and 17 positions.

This advantageous aspect may be better appreciated if considering the difficulties found during the synthesis of Desogestrel reported in scheme 2, where the simultaneous presence of two ketone groups at the 17 and 11 positions, in the analogous compound of formula IX, requires a not easy chemical manipulation of that substrates in order to obtain a selective protection of only one of the two functional groups.

From an experimental point of view such a regioselectivity is never complete and requires a difficult purification procedure of the complex admixture of products.

The above regioselective reduction (a) can be performed by adding the substrate XIIa, dissolved into an organic solvent, to an admixture of alkaline borohydride, a strong organic acid and a $C_1$-$C_3$ organic acid, preferably sodium borohydride, trifluoroacetic acid and acetic acid, in a temperature range generally between 0° C. and +25° C., preferably at around 20° C., leading to the compound XIVa with yields usually between 57 and 76%.

The alkaline borohydrides which can be advantageously used in this step are represented by sodium and potassium borohydride, preferably by sodium borohydride.

The strong organic acid may be any organic acid with a pKa value lower than 2, preferably a derivative of the acetic acid or methansulfonic acid, such as for example trifluoroacetic, difluoroacetic or trifluoromethansulfonic acid, more preferably trifluoroacetic acid.

The $C_1$-$C_3$ organic acids which can be used in admixture with the trifluoroacetic acid are formic, acetic and propionic acid, preferably acetic acid.

Solvents suitable for dissolving the substrate XIIa in this synthetic step are generally the chlorinated hydrocarbons, simple cyclic or acyclic ethers and polyethers, preferably dichloromethane, tetrahydrofuran or diglyme, more preferably dichloromethane, used alone or in admixture thereof.

Such solvents may be used for dissolving the substrate as such or, optionally, in admixture with acetic or trifluoroacetic acid up to a final concentration of acid used at around 2% by volume. In this step the alkaline borohydride is generally used in excess with respect to the substrate XIIa; the ratio between the moles of borohydride and moles of substrate is preferably comprised between 8 and 2, more preferably between 5,5 and 6,5.

The acids are preferably used in excess with respect to the substrate XIIa and in a reciprocal ratio by volume comprised between 2:1 and 1:2, more preferably in a ratio by volume of 1:1.

In a preferred embodiment the regioselective reduction is performed with about 6 moles of sodium borohydride per mole of compound of formula XIIa, trifluoroacetic and acetic acid in a ratio by volume of 1:1, in a dichloromethane solution, at a reaction temperature between 0° C. and 25° C.

The regioselective reaction of reduction of the carbonyl group at 3 to methylene group, in the presence of a second carbonyl function at 17, above described can be applied to analogous steroidal substrates 3,17 diketo substituted as herein after depicted:

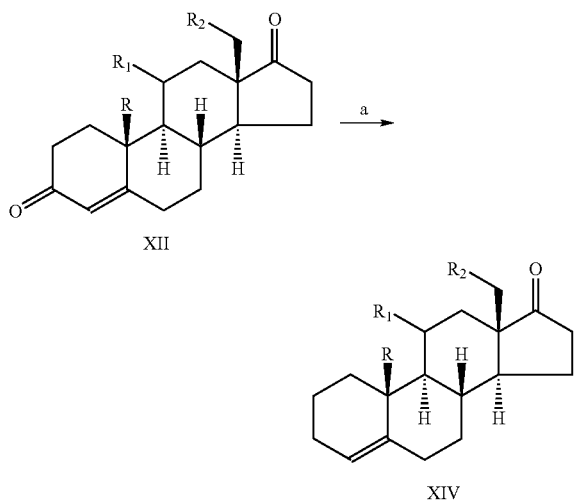

Scheme 5a in which R and $R_2$ represent H or $CH_3$, and $R_1$ represents H or OH.

In general the experimental conditions of this reaction of reduction are similar to those already described for the reduction of compound XIIa.

The corresponding products 3-deoxy-17-keto substituted of formula XIV so prepared may found a useful application as intermediates in the manufacturing of therapeutically active steroids such as for example linestrenol.

In a preferred embodiment, the above reaction of reduction is performed on the compound of formula XIIa, in which R=H, $R_1$=OH and $R_2$=$CH_3$, to give the compound of formula XIVa, intermediate useful for the preparation of Desogestrel, in which R, $R_1$ and $R_2$ have the same meanings.

The intermediate XIVa is then protected at the 17 position as a ketal (b) and subjected to an oxidative reaction of the hydroxy group at the 11 position (c) and subsequently, at the so formed carbonyl level, to an olefination reaction (d) as herein below represented:

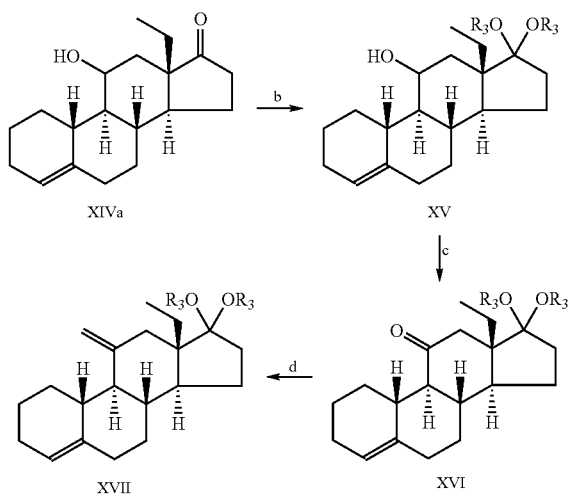

Scheme 6 in which $R_3$ represents a $C_1$-$C_5$ alkyl or the two $R_3$ groups together represent a —$(CH_2)_n$— chain, wherein n is an integer from 2 to 4, optionally substituted by one or more methyls.

In the sequence above, preferred intermediates are the compounds of formula XV, XVI and XVII protected as cyclic ketals, namely the intermediates in which the two $R_3$ groups together form a chain —$(CH_2)_n$— as previously defined, even more preferably the cyclic ketals in which n=3, according to the following scheme:

Scheme 6a

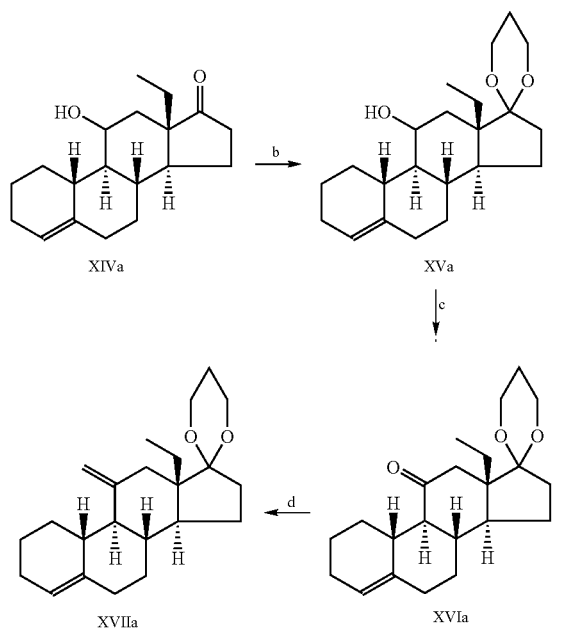

The intermediates, XVIa and XVIIa, in which the two $R_3$ groups together form a —$(CH_2)_3$— chain, are new and represent another object of the present invention.

The transformation (b) of the compound of formula XIVa into the ketal of formula XV, is performed under classical conditions of ketalization (see T. Green in Protective groups in organic synthesis, third edition, page 297), for example by reaction of the selected alcohol or diol, in amounts generally higher than the stoichiometric ones, in the presence of an orthoester in excess and of an acidic catalyst.

In one of its preferred embodiments such a reaction is performed in a range of temperature between 10 and 50° C., preferably at about 40° C. in the presence of 4-7 equivalents of 1,3-propandiol, of 2-4 moles of triethylorthoformate per mole of substrate and of p-toluensulfonic acid in catalytic amount, generally obtaining variable yields from 50 to 80%.

The oxidation reaction (c) of the hydroxy group, present at the 11 position, of the compound XV to give the compound of formula XVI, can be effected by following the classical oxidative methods of alcohols to ketones, for example according to what described by Carey e Sundberg, in Advanced organic chemistry, third edition, pages 615-624.

Preferably the above oxidation, whose yields generally ranges from 50 to 70%, is performed by using chromium-based oxidants, such as 10% chromic acid in 9/1 pyridine/water (Conforth reagent), pyridinium chlorochromate or 4-dimethylaminopyridinium chlorochromate.

The oxidation reaction is usually performed in an organic solvent selected among dichloromethane, admixtures of dichloromethane and water in the presence of a phase transfer (for ex. tetramethylammonium hydrogensulfate) or in pyridine, preferably in dichloromethane, at a concentration of the substrate XV preferably comprised between 0.05 and 0.2 molar and at a temperature generally comprised between 0° C. and 15° C.

The olefination reaction (d) of the compound of formula XVI to give the compound of formula XVII can be performed by a classical Wittig reaction, using methyltriphenyl phosphonium iodide or chloride as phosphonium salt, preferably methyltriphenylphosphonium iodide, in excess, preferably with a molar ratio of about 3:1 with respect to the substrate, and in an aprotic polar solvent such as dimethylsulfoxide, or in an ether such as t-butylmethyl ether or tetrahydrofuran, preferably in dimethylsulfoxide. The base used for preparing the ylide can be a strong organic or inorganic base commonly used in this kind of reactions, for example butyl lithium or sodium hydride, preferably sodium hydride, in ratios generally from 1.1 to 1.5 per mole of phosphonium salt.

The temperature at which the reaction between the ylide and the compound of formula XVI is performed, may be between 40° C. and 90° C., preferably at about 80° C.

In a particularly preferred embodiment the conversion from XIVa to XVIIa comprises:

the protection of the carbonyl group (B) performed in the presence of 4-7 equivalents of 1,3-propandiol, of 2-4 moles of triethylorthoformate per mole of substrate XIVa and of p-toluensulfonic acid in catalytic amount, at a temperature between 10 and 50° C., preferably at about 40° C.

the oxidation reaction (c) performed with a chromium based oxidant selected among 10% chromic acid in 9/1 pyridine/water (Conforth reagent), pyridinium chlorochromate and 4-dimethylaminopyridinium chlorochromate in an organic solvent selected among dichloromethane, pyridine and admixtures of dichloromethane and water, in the presence of a phase transfer, at a concentration of substrate XV between 0.05 and. 0.2 molar and at a temperature between 0° C. and 15° C.;

the olefination reaction (d) by reaction with an excess of methyltriphenylphosphonium iodide or chloride, in an aprotic polar solvent or in an ether, in the presence of a strong base, in ratios between 1.1 and 1.5 moles per mole of phosphonium salt, at a temperature between 40° C. and 90° C.

The use the compounds of formula XIIa, XIVa and XV, for the preparation of Desogestrel, is new and inventive and represents a further object of the present invention.

The so obtained compound of formula XVII is then deprotected (e) under classical conditions (see for example the already mentioned T. Green in Protective groups in organic synthesis), to give the known intermediate of formula XVIII which, submitted to an ethinylation reaction at 17 (f) as already described in the literature (see for example the already mentioned patent U.S. Pat. No. 5,831,104), furnishes Desogestrel, according to the following scheme:

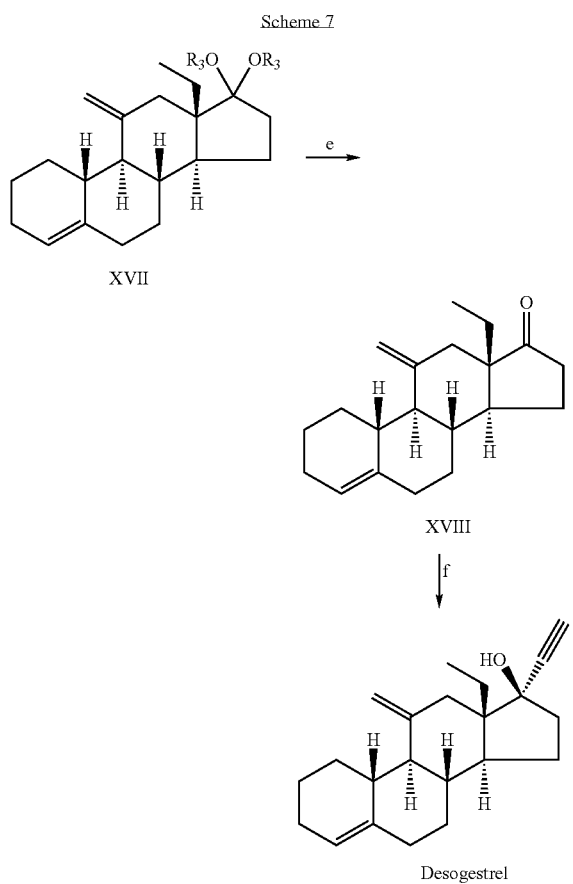

Scheme 7

XVII

XVIII

Desogestrel

Following the above described synthetic route we have prepared the intermediate of formula XVIII and Desogestrel which show chemical-physical features in compliance with the data reported in the literature (S. Schwarz et al. Tetrahedron, vol. 50, N°36, pages 10709-10720, 1994).

With the aim to better illustrate the present invention the following examples will now be given.

EXAMPLE 1

Preparation of 13-ethyl-11-hydroxy-gon-4-ene-3,17-dione (compound XIIa) from 13-ethyl-gon-4-en-3,17-dione (compound XI)

The starter was prepared in a 5.0 l flask. The medium was prepared starting from 200 ml of a 16.5% glucose solution and 800 ml of an aqueous solution having the following composition:
1. atomized corn steep=7.00 g/l
2. anhydrous glucose=33.00 g/l
3. potassium phosphate monobasic=1.00 g/l
4. potassium phosphate dibasic=2.00 g/l
5. sodium nitrate=2.00 g/l
6. potassium chloride=0.5 g/l
7. magnesium sulfate heptahydrate=0.5 g/l
8. iron sulfate heptahydrate=0.02 g/l The two solutions were separately sterilized (121° C. for 30') and then collected for making the complete medium.

Each flask was inoculated with a slant of *Aspergillus ochraceous* (strain F9-Poli Collection) of about 18 cm$^2$ of felt, taken from a slant of Potato Dextrose Agar homogenized in a Potter with 5 ml of physiological solution; 3 flasks were inoculated for a total of 3.0 l of cultural broth. The incubation of the culture was performed on a rotating shaker at 120 rpm at a temperature of 27+/−1° C.

3.0 l of cultural broth were transferred from three flasks into a 5.0 l starter bottle.

A first vegetative step was performed in a 200 liters bioreactor and a second growing step in a 1200 liters bioreactor.

The enzymatic activity was induced by addition of 240 ml of a 100 g/l solution of 13-ethyl-gon-4-en-3,17-dione (compound XI) in N,N-dimethylformamide (DMF) to the cultural broth after 8-16 hours from starting the second growing step. After 3-6 hours from the end of the addition of the starter solution, a solution of the substrate, prepared from 4.0 kg of 13-ethyl-gon-4-en-3,17-dione (compound XI) in DMF (40.0 liters) was added. The addition was performed continuously for 23-25 hours (33.33 ml/min).

At the end of this period, the fermentation broth was filtered on dicalite (6 kg), washing the obtained cake with ethyl acetate (150 l). The filtered aqueous phase and the organic phase were collected, placed under stirring for 15', and then separated by settling. The aqueous phase was re-extracted withy ethyl acetate (2×150 l). The organic extracts were collected and concentrated up to a residual volume of 3-4 liters. Such a solution was maintained under stirring at a temperature of 14-16° C. for 8 hours; a precipitate was obtained, which was retrieved by filtration and dried under vacuum at a temperature of 60° C. for 8 hours. The raw precipitate so obtained was dispersed in dichloromethane (13 kg per kg of dried product) and filtered. The so obtained filtrate was concentrated under vacuum up to a residual volume of 5-7 liters; hexane (26 kg) was slowly added to such a solution, kept under stirring at a temperature of 14-16° C. At the end of the addition the obtained heterogeneous suspension was kept under stirring at a temperature of 14-16° C. for 30' then the precipitate was retrieved by filtration.

A humid product was thus obtained, which was dried under vacuum at a temperature of 60° C. for 8 hours to give 1.6 Kg of 13-ethy-11-hydroxy-gon-4en-3,17-dione (compound XIIa).

For analytical purposes, the obtained product was re-crystallized from dichloromethane-hexane to give a sample with the following analytical characteristics:

TLC on silica gel plate using 9/1 dichloromethane/methanol as eluent: r.f. 0.62 GC (FID) HP-5 30 m×0.25 mm column (0.25 mm film thickness); nitrogen as carrier; injector temperature 300° C., oven temperature: 230° C.×5' then up to 280° C. (5° C./min), such a temperature was kept for 5': rt of 13' 30". Mass Spectrum (m/z): 303 (m+1), 302 (molecular ion), 285 (m-17), 274 (m-28), 255 (m47) $^1$H-NMR (500 MHz) in CDCl$_3$, some of the diagnostic signals can be thus assigned:

| δ (ppm) | Attribution | 1H-Multiplicity | Integral |
|---|---|---|---|
| 0.78 | —CH$_2$—CH$_3$ | t, J = 7.5 Hz | 3H |
| 1.05-1.25 | 2CH$_2$; 9C$\overline{H}$; 7CH$_2$ | complex system | 3H |
| 1.30-1.52 | 14CH; —C$\overline{H_2}$—CH$_3$ | complex system | 3H |
| 1.52-1.70 | 15CH$_2$; 8C$\overline{H}$ | complex system | 2H |
| 1.87-1.95 | 15CH$_2$ | m | 1H |
| 1.95-2.02 | 7CH$_2$ | m | 1H |
| 2.09-2.20 | 16CH$_2$ | m | 1H |
| 2.20-2.52 | 16CH$_2$; 10CH; 12CH$_2$; 2CH$_2$; 1CH$_2$; 6CH$_2$ | complex system | 10H |
| 3.82 | 11CH—O | m | 1H |
| 5.84 | 4=CH | s, broad | 1H |

EXAMPLE 2

Preparation of 13-ethyl-11-hydroxy-gon-4-en-17-one (compound XIVa) from 13-ethyl-11-hydroxy-gon-4-en-3,17-dione (compound XIIa)

A suspension made of sodiumborohydride (152 g) in dichloromethane (0.60 liters) was added to a mixture of trifluoroacetic acid (1.13 liters) in acetic acid (1.13 liters) under stirring at a temperature of 0° C. in about 2 hours. At the end of the addition of the suspension of sodiumborohydride, a solution made of 13-ethyl-11-hydroxy-gon-4en-3,17-dione (201.00 g; 0.66 moles; compound XVIa) in dichloromethane (660 ml) was added to the reaction mixture under stirring at the temperature of 0° C. The reaction mixture was kept under stirring at a temperature of 20° C. for 20' then it was cooled at the temperature of 0° C. and 4 liters of an aqueous admixture of sodium hydroxide were added (this solution was prepared from 1 liter of water and 3 liters of 30% sodium hydroxide). The reaction was then extracted with dichloromethane (3×2.5 liters), the organic extracts dehydrated on sodium sulfate, filtered and concentrated under vacuum to give 210.20 g of raw 13-ethyl-11-hydroxy-gon-4-en-17-one (compound XIVa). Such a crude may be further purified by silica gel chromatography (1/5 p/p) by eluting under a gradient of polarity, by using an admixture of toluene and ethyl acetate as mobile phase: by eluting with 9/1 toluene/ethyl acetate 144.67 g (0.50 moles; yields 76%) of pure compound XIVa were obtained, with the following analytical characteristics:

TLC on silica gel plate using 9/1 dichloromethane/methanol as eluent: r.f. 0.77 GC (PMD) HP-5 30 m×0.25 mm column (0.25 mm film thickness); nitrogen as carrier; oven temperature: 230° C.×5' then up to 280° C. (5° C./min), such a temperature was kept for 5': rt of 13' 30". $^1$H-NMR (500 MHz) in $CDCl_3$, some of diagnostic signals can be so assigned (values in ppm): 1.02 (—CH2-CH3, t, J=7.5 Hz, 3H), 2.82 (d, J=12 Hz, 1H), 3.80 (11CH—O, m, 1H), 5.40 (4=CH, s, broad).

EXAMPLE 2 BIS

Preparation of 13-ethyl-11-hydroxy-gon-4-en-17-one (compound XIVa) from 13-ethyl-11l-hydroxy-gon-4-en-3,17-dione (compound XIIa)

Applying the same procedure described in the example 2, but using difluoroacetic acid and methansulfonic acid, in the same molar ratio, instead of trifluoroacetic acid the following results were obtained:

| Acid | Yields of compound XIV (molar %) after chromatography |
|---|---|
| Difluoroacetic acid | 35 |
| Trifluoromethansulfonic acid | 38 |

EXAMPLE 3

Preparation of 13-ethy-11-hydroxy-17,17-(1,3-propylendiox)-gon-4-ene (compound XVa) from 13-ethyl-11-hydroxy-gon-4-en-17-one (compound XIVa)

8.69 g (30.17 mmoles) of 13-ethyl-11-hydroxy-gon-4-en-17-one (compound XIVa) were dissolved under stirring at room temperature in 17.4 ml of triethylorthoformate and 12.00 ml of 1,3-propandiol. 518 mg of p-toluensulfonic acid monohydrate were added to the reaction admixture and the stirring was carried on at the temperature of 40° C. for 6 hours. At the end of this period, the reaction mixture was cooled at room temperature and spilled into 43 ml of a saturated solution of sodium bicarbonate, 207 ml of toluene were added and the aqueous phase was separated and re-extracted with toluene (2×40 ml). The organic extracts were dehydrated on sodium sulfate, filtered and evaporated under vacuum to give an oily residue of 15.8 g.

For analytical purposes such a crude was further purified by chromatography on alumina (p/p ratio 1/1) by eluting under an increasing gradient of polarity with hexane/ethyl acetate: by eluting with 8/2 hexane/ethyl acetate was obtained a pure sample of the compound XVa with the following analytical characteristics:

TLC on silica gel plate using 8/2 toluene/ethyl acetate as eluent: rf 0.57 $^1$H-NMR (60 MHz) in $CDCl_3$, some of the diagnostic signals can be so assigned (values in ppm): 0.90 (—CH2-CH3, m), 3.45-4.20 (11CH—O e 2-CH2O, complex system, 5H), 5.50 (4=CH, s, broad)

EXAMPLE 4

Preparation of 13-ethyl-17,17-(1,3-propylendioxy)-gon-4-ene-11-one (compound XVIa) from 13-ethyl-11-hydroxy-17,17-(1,3-propylendioxy)-gon-4-ene (compound XVa)

1.5 g (4.33 mmoles) of 13-ethyl-11-hydroxy-17,17-(1,3-propylendioxy)-gon-4-ene (compound XVa) were dissolved in dichloromethane (60 ml) under stirring at the temperature of 10° C. 0° C. 4.5 ml of Conforth's reagent (10% $CrO_3$ in 9/1 pyridine/water) were added to the so obtained solution and the stirring of the reaction mixture was continued for 15 hours at room temperature. After this period the reaction was worked-up: isopropyl alcohol was added (3.0 ml) and the stirring of the reaction admixture was continued for other 30'. The reaction admixture was then filtered on Florisil (10 g) washing the cake with 50 ml of dichloromethane. The filtered organic phases were collected and concentrated under vacuum to furnish an oil which is taken up in toluene (10 ml), the so obtained solution was evaporated under vacuum up to an oily residue and then taken up again with toluene (10 ml) and then re-evaporated to dryness: in such a way 1.04 g (3.03 mmoles) of raw intermediate XVIa were obtained.

For analytical purposes such a crude was further purified by chromatography on alumina (p/p ratio 1/15) eluting under a gradient of increasing polarity with hexane/ethyl acetate: by eluting with 95/5 hexane/ethyl acetate a pure sample of compound XVIa was obtained, some analytical characteristics of which are reported:

TLC on silica gel plates using 8/2 toluene/ethyl acetate as eluent: rf 0.68 $^1$H-NMR (500 MHz) in $CDCl_3$, some of the diagnostic signals can be so assigned (values in ppm): 1.02 (—CH2-CH3, t, J=7.4 Hz), 2.45 (d, 12CH2, J=12.1 Hz 1H), 2.66 (d, 12CH2, J=12.1 Hz, 1H), 3.64-4.02 (2-CH2O, complex system, 4H), 5.44 (4=CH, s, broad)

EXAMPLE 4BIS

Preparation of 13-ethyl-17,17-(1,3-propylendioxy)-gon-4-ene-11-one (compound XVIa) from 13-ethyl-11-hydroxy-17,17-(1,3-propylendioxy)-gon-4-ene (compound XVa)

Similarly to what described in the example 4 the oxidation reaction may be performed by using 4-dimethylaminopyridinium chlorochromate as alternative to the Conforth's reagent. The reaction performed by adding the reagent to the substrate solution (711 bag of compound Xva; 2.06 mmoles) in dichloromethane (10 ml) under stirring at room temperature for 40 hours led, after the usual work-up, to 390 mg (1.13 mmoles) of compound XVIa.

The chemical-physical characteristics of the obtained sample were in compliance with those reported for the example 4.

EXAMPLE 5

Preparation of 13-ethyl-11-methylen-17,17-(1,3-propilendioxy-gon-4-ene (compound XVIIa) from 13-ethyl-17,17-(1,3-propylendioxy)-gon-4ene-11-one (compound XVIa)

4.46 g of methyltriphenylphosphonium iodide were added to a suspension made of 0.422 g of sodium hydride (60% oily suspension) in anhydrous dimethylsulfoxide (6.02 ml) under stirring at room temperature. The reaction mixture was kept under stirring at the temperature of 80° C. for 90' then a solution of 1.15 g (3.34 mmoles) of 13-ethyl-17,17-(1,3-propylendioxy)-gon-4-ene-11-one (compound XVIa) in 1.60 ml of anhydrous toluene was added. the reaction was kept under stirring at the temperature of 80° C. under inert atmosphere for 15 hours then it was spilled into water cooled at a temperature of about 2° C. The mixture so obtained was extracted with dichloromethane (3×20 ml) and the separated organic phase was washed three times with a saturated solution of sodium chloride, dehydrated on sodium sulfate, filtered and evaporated to give an oily crude of about 3.60 g. Such a crude was purified by chromatography on alumina (p/p ratio 1/15) eluting with hexane: by eluting with hexane a pure sample of 0.74 g (2.17 mmoles; yields 65%) of compound XVIIa was obtained, some analytical characteristics of which are reported:

TLC on silica gel plate using 8/2 toluene/ethyl acetate as eluent: rf 0.85 $^1$H-NMR (500 MHz) in $CDCl_3$ , some of the diagnostic signals can be so assigned (values in ppm): 0.96 (—CH2-CH3, t, J=7. Hz, 3H), 2.20 (d, 12CH2, J=12.1 Hz 1H), 2.40 (d, 12CH2, J=12.1 Hz, 1H), 3.64-4.00 (2-CH2O, complex system, 4H), 4.72 (=CH2, s, 1H), 4.92 (=CH2, s, 1H), 5.44 (4=CH, s, broad)

EXAMPLE 6

Preparation of 13-ethyl-11-methylen-gon-4-ene (compound XVII) from 13-ethyl-11-methylen-17,17-(1,3-propilendioxy)-gon-4-ene (compound XVIIa)

1.3 g (3.79 mmoles) of 13-ethyl-11-methylen-17,17-(1,3-propylendioxy)-gon-4-ene (compound XVIIa) were dissolved in acetone (21 ml) under stirring at room temperature. 250 mg of p-toluensulfonic acid monohydrate were added to the solution so obtained and the stirring at room temperature was continued for 17 hours. After this period a saturated solution of sodium bicarbonate (21 ml) was added to the reaction mixture and the organic solvent was evaporated under vacuum. The so obtained aqueous suspension was extracted with dichloromethane (3×30 ml) and the organic extracts dried on sodium sulfate, filtered and evaporated under vacuum to give 0.88 g (3.11 mmoles; yields 82%) of the intermediate 13-ethyl-11-methylen-gon-4-ene (compound XVIII).

For analytical purposes such compound can be purified by crystallization from ethanol to give a product with the following analytical characteristics:

TLC on silica gel plate using 8/2 toluene/ethyl acetate as eluent: rf 0.72 $^1$H-NMR (500 MHz) in $CDCl_3$, some of the diagnostic signals can be so assigned (values in ppm): 0.75 (—CH2-CH3, t, J=7.5 Hz), 2.58 (12CH2, 12,3 Hz, 1H), 4.80 (=CH2, s, 1H), 4.90 (=CH2, s, 1H), 5.50 (4=CH, s, broad). m.p.=99-101° C.

EXAMPLE 7

Preparation of Desogestrel from 13-ethyl-11-methylen-gon-4-ene (compound XVII)

100 g (0.35 moles) of 13-ethyl-11-methylen-gon-4-ene (compound XVIII) were dissolved in anhydrous dimethylsulfoxide (3 liters) under stirring at room temperature. 430 g of lithium acetylide complexed with ethylendiamine were added to the so obtained solution and the stirring at room temperature was carried on for 21 hours. After this period the reaction was spilled in water cooled at a temperature of 2° C. (3 liters) then a 10% aqueous solution of acetic acid was added (7 liters) and the aqueous phase was extracted with dichloromethane (3×2 liters). The organic extracts were subsequently washed with a saturated solution of sodium bicarbonate (2 liters) and then with a saturated solution of sodium chloride. The organic phase was then dehydrated on sodium sulfate, filtered and evaporated to dryness to give 96.24 g (0.31 moles; yields 89%) of Desogestrel.

The product thus obtained can be further purified by crystallization from hexane and then from acetone/water to give a sample with the following chemical-physical characteristics:

$[\alpha]_D$=+57° (c=0.01 chloroform) DSC melting endotherm at 111.39° C. (rate of heating 5° C./min) IR (2% KBr) values in $cmna^{-1}$: 3541.45 (O—H stretching) 3284.98 (stretching acetylenic C—H) 3090.14 (weak) 2103.48 (weak, C≡C stretching) 1639.94 (medium) 1033.39 and 1042.91 (C—O stretching) 909.80 and 897.87 (out of plane, =CH2) Calculated elementary analysis for $C_{22}H_{30}O$: theoretical values: C, 85.11; H, 9.74; O, 5.15; Found values: C, 85.09; H, 9.72 Mass Spectrum (m/z): 311 (m+1), 310 (molecular ion), 294 (m–16), 282 (m–28), 264 (m–46)

| | $^1$H-NMR (500 MHz) in $CDCl_3$ | | |
|---|---|---|---|
| δ (ppm) | Attribution | 1H-Multiplicity | Integral |
| 8.70-9.70 | 7CH$_2$ | m | 1H |
| 1.10 | —CH$_2$—CH$_3$ | t J = 7.5 Hz | 3H |
| 1.70-1.17 | 1CH$_2$ | m | 1H |
| 1.26-1.42 | 9CH; 8CH; 15CH$_2$ | complex system | 4H |
| 1.42 | —CH$_2$—CH$_3$ | q J = 7.5 Hz, | 2H |
| 1.55-1.68 | 7CH$_2$; 3CH$_2$ | complex system | 3H |
| 1.72-1.80 | 14CH | m | 1H |
| 1.86-1.98 | 6CH$_2$; 2CH$_2$ | m | 3H |
| 2.03-2.15 | 16CH$_2$ | m | 1H |
| 2.16-2.28 | 10CH; 1CH$_2$; 6CH$_2$; 12CH$_2$ | complex system | 4H |
| 2.58 | acetylenic CH | s | 1H |
| 2.60 | 12CH | d J = 12.4 Hz | 1H |
| 4.76 | =CH$_2$ | s | 1H |
| 4.96 | =CH$_2$ | s | 1H |
| 5.44 | 4=CH | s, broad | 1H |

| ¹³C-NMR (125.721 MHz) in CDCl₃ | | | |
|---|---|---|---|
| δ¹³C(ppm) | Attribution | Frequency | Intensity |
| 148.2076 | C-11 | 18638.454 | 2.267 |
| 140.5835 | C-5 | 17679.647 | 1.945 |
| 122.0206 | C-4 | 15345.200 | 4.642 |
| 109.1980 | =CH₂ | 13732.644 | 4.6228 |
| 88.5589 | —C≡CH | 11137.081 | 2.004 |
| 81.8279 | C-17 | 10290.601 | 1.472 |
| 74.7362 | —C≡CH | 9398.758 | 4.300 |
| 55.3591 | C-9 | 6961.911 | 5.936 |
| 53.1152 | C-14 | 6679.716 | 6.090 |
| 51.1012 | C-13 | 6426.440 | 1.755 |
| 43.2883 | C-8 | 5443.900 | 5.708 |
| 41.3149 | C-12 | 5195.717 | 5.533 |
| 40.4963 | C-16 | 5092.782 | 5.747 |
| 37.2807 | C-10 | 4688.386 | 5.766 |
| 36.2203 | C-6 | 4555.036 | 5.794 |
| 32.4107 | C-7 | 4075.935 | 5.276 |
| 29.7885 | c-1 | 3746.178 | 5.791 |
| 26.3767 | C-2 | 3317.109 | 5.802 |
| 22.6318 | C-3 | 2846.148 | 5.944 |
| 22.5902 | C-15 | 2840.920 | 4.822 |
| 20.5044 | CH₂—CH₃ | 2578.610 | 5.001 |
| 9.8278 | CH₂—CH₃ | 1235.935 | 3.717 |

The invention claimed is:

1. A process for the preparation of Desogestrel which comprises the regioselective reduction of the compound of formula

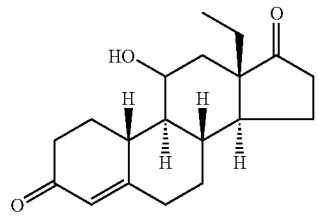

XIIa to give the compound of formula

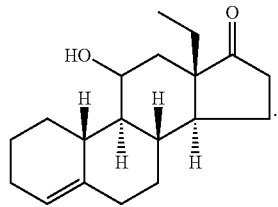

XIVa

2. A process according to claim 1 in which said reduction is performed in the presence of an alkaline borohydride, a strong organic acid and a C₁-C₃ organic acid.

3. A process according to claim 2 in which said borohydride is sodium borohydride, said strong organic acid is trifluoroacetic acid and said C₁-C₃ organic acid is acetic acid.

4. A process according to claim 2 in which said reduction is performed in an organic solvent selected among dichloromethane, tetrahydrofuran or diglyme.

5. A process according to claim 2 in which the ratio between the moles of borohydride and the moles of compound XIIa is between 8 and 2.

6. A process according to claim 3 in which trifluoroacetic acid and acetic acid are used in a ratio by volume from 2:1 to 1:2.

7. A process according to claim 1 in which said reduction is performed with about 6 moles of sodium borohydride per mole of compound XIIa, trifluoroacetic acid and acetic acid in a ratio by volume of 1:1, in dichloromethane and at a temperature of reaction between 0° C. and 25° C.

8. A process according to claim 1 which further comprises:
    (b) the protection of the carbonyl group of the compound of formula XIVa to give the protected compound of formula

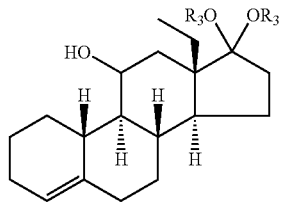

XV in which
    R₃ represents a C₁-C₅ alkyl group or the R₃ groups together represent a —(CH₂)ₙ— chain wherein n is an integer from 2 to 4, optionally substituted by one or more methyl groups;
    (c) the subsequent oxidation reaction of the protected compound of formula XV to give the compound of formula

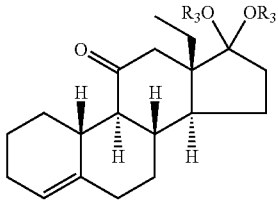

XVI in which R₃ has the above reported meanings;
    (d) the subsequent olefination reaction of the compound of formula XVI to give the compound of formula

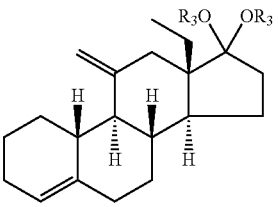

XVII in which R₃ has the above reported meanings.

9. A process according to claim 8 in which the two R₃ groups together form a —(CH₂)ₙ— chain wherein n is equal to 3.

10. A process according to claim 8 in which the protection of the carbonyl group (b) is performed in the presence of 4-7 equivalents of 1,3-propandiol, of 2-4 moles of triethylorthoformate per mole of substrate XIVa and of p-toluensulfonic acid in a catalytic amount, at a temperature between 10 and 50° C.

11. A process according to claim 8 in which the oxidation reaction (c) is performed with a chromium based oxidant selected among 10% chromic acid in 9/1 pyridine/water (Conforth's reagent), pyridinium chlorochromate and 4-dimethylaminopiridinium chlorochromate, in an organic solvent selected among dichloromethane or admixtures of dichloromethane and water, in the presence of a phase transfer, or pyridine, at a concentration of substrate XV between 0.05 and 0.2 molar and at a temperature between 0° C. and 15° C.

12. A process according to claim 8 in which the olefination reaction (d) is performed by reaction with methyltriphenylphosphonium iodide or chloride, in a polar aprotic solvent or in an ether, in the presence of 1.1-1.5 moles of a strong base per mole of phosphonium salt, at a temperature between 40° C. and 90° C.

13. A process according to claim 8 which further comprises:
(e) the deprotection reaction of the compound of formula XVII to give the compound of formula

XVIII

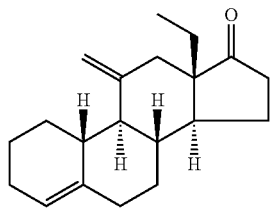

(f) the subsequent ethinylation reaction at the 17 position of the compound of formula XVIII to give Desogestrel of formula

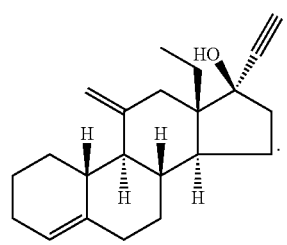

14. A process for the preparation of Desogestrel which comprises:
(b) the protection of the carbonyl group of the compound of formula XIVa

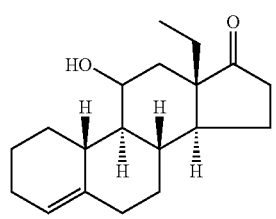

to give the protected compound of formula

XV

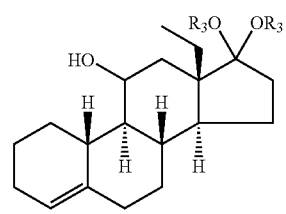

in which
R$_3$ represents a C$_1$-C$_5$ alkyl or the two R$_3$ groups together represent a —(CH$_2$)$_n$— chain wherein n is an integer from 2 to 4, optionally substituted by one or more methyl groups;

(c) the subsequent oxidation reaction of the protected compound of formula XV to give the compound of formula

XVI

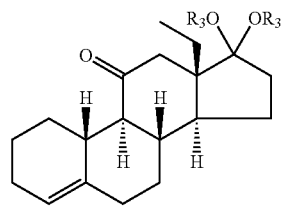

in which R$_3$ has the above reported meanings;
(d) the subsequent olefination reaction of the compound of formula XVI to give the compound of formula

XVII

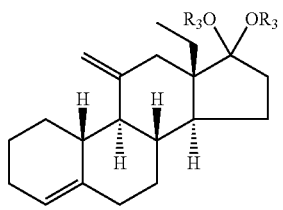

in which R$_3$ has the above reported meanings.

15. The compounds of formula

XIVa

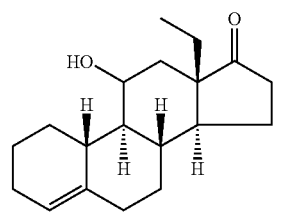

XVa

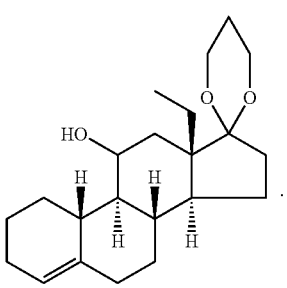

16. A process for the preparation of a compound of formula

XIV

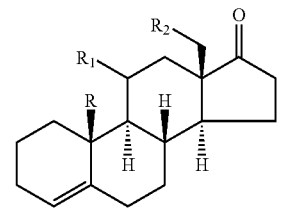

in which

R and $R_2$ represent H or $CH_3$, and $R_1$ represents H or OH, by regioselective reduction of the compound of formula

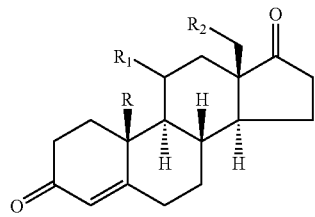

XII in which R, $R_1$ and $R_2$ have the meanings reported above.

17. A process according to claim 16 wherein R=H, $R_1$=OH and $R_2$=$CH_3$.

18. A process according to claim 16 in which said reduction is performed in the presence of an alkaline borohydride, a strong organic acid and a $C_1$-$C_3$ organic acid and in which said reduction is performed in an organic solvent selected from the group consisting of dichloromethane, tetrahydrofuran or diglyme, in which the ratio between the moles of borohydride and the moles of compound XIIa is between 8 and 2, in which trifluoroacetic acid and acetic acid are used in a ratio by volume from 2:1 to 1:2, and in which said reduction is performed with about 6 moles of sodium borohydride per mole of compound XIIa, trifluoroacetic acid and acetic acid in a ratio by volume of 1:1, in dichloromethane and at a temperature of reaction between 0° C. and 25° C., wherein compound XIIa is a compound of formula

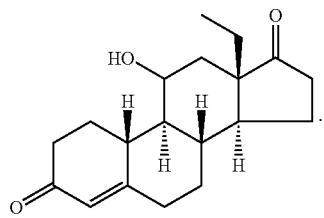

XIIa

19. A method of preparing Desogestrel comprising providing one or more compounds of formula

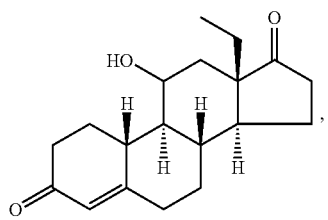

XIIa

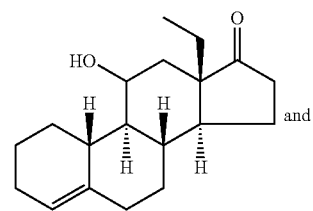

XIVa and

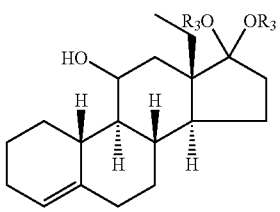

XV as intermediates and reacting said intermediates to produce Desogestrel.

20. A process according to claim 17 in which said reduction is performed in the presence of an alkaline borohydride, a strong organic acid and a $C_1$-$C_3$ organic acid and in which said reduction is performed in an organic solvent selected from the group consisting of dichloromethane, tetrahydrofuran or diglyme, in which the ratio between the moles of borohydride and the moles of compound XIIa is between 8 and 2, in which trifluoroacetic acid and acetic acid are used in a ratio by volume from 2:1 to 1:2, and in which said reduction is performed with about 6 moles of sodium borohydride per mole of compound XIIa, trifluoroacetic acid and acetic acid in a ratio by volume of 1:1, in dichloromethane and at a temperature of reaction between 0° C. and 25° C., wherein compound XIIa is a compound of formula

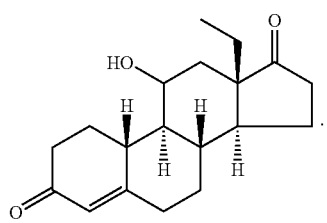

XIIa

21. The process according to claim 2 in which said reduction is performed in an organic solvent comprising dichloromethane.

22. The process according to claim 2 in which the ratio between the moles of borohydride and the moles of compound XIIa is between 5.5 and 6.5.

23. The process according to claim 3 in which trifluoroacetic acid and acetic acid are used in a ratio by volume of 1:1.

24. The process according to claim 10 in which the protection of the carbonyl group (b) is performed at a temperature of about 40° C.

25. The process according to claim 18 wherein the alkaline borohydride is sodium borohydride.

26. The process according to claim 18 wherein the strong organic acid is trifluoroacetic acid.

27. The process according to claim 18 wherein the $C_1$-$C_3$ organic acid is acetic acid.

28. The process according to claim 20 wherein the alkaline borohydride is sodium borohydride.

29. The process according to claim 20 wherein the strong organic acid is trifluoroacetic acid.

30. The process according to claim 20 wherein the $C_1$-$C_3$ organic acid is acetic acid.

* * * * *

UNITED STATES PATENT AND TRADEMARK OFFICE
CERTIFICATE OF CORRECTION

PATENT NO. : 7,667,056 B2  Page 1 of 1
APPLICATION NO. : 10/523058
DATED : February 23, 2010
INVENTOR(S) : Grisenti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1216 days.

Signed and Sealed this

Twenty-eighth Day of December, 2010

David J. Kappos
*Director of the United States Patent and Trademark Office*

(12) INTER PARTES REEXAMINATION CERTIFICATE (0305th)
United States Patent
Grisenti et al.

(10) Number: US 7,667,056 C1
(45) Certificate Issued: Sep. 27, 2011

(54) PROCESS AND NEW INTERMEDIATES FOR THE PREPARATION OF STEROIDS WITH A PROGESTOGEN ACTIVITY

(75) Inventors: Paride Grisenti, Milan (IT); Fabio Pecora, Milan (IT); Elisa Verza, Milan (IT); Massimo Leoni, Milan (IT); Laura Bossi, Milan (IT)

(73) Assignee: Poli Industria Chimica SpA, Milan (IT)

Reexamination Request:
No. 95/001,423, Aug. 25, 2010

Reexamination Certificate for:
Patent No.: 7,667,056
Issued: Feb. 23, 2010
Appl. No.: 10/523,058
Filed: Feb. 2, 2005

Certificate of Correction issued Dec. 28, 2010.

(22) PCT Filed: Jul. 31, 2003
(86) PCT No.: PCT/EP03/08505
§ 371 (c)(1), (2), (4) Date: Feb. 2, 2005
(87) PCT Pub. No.: WO2004/014934
PCT Pub. Date: Feb. 19, 2004

(51) Int. Cl.
C07J 1/00 (2006.01)
C07J 21/00 (2006.01)

(52) U.S. Cl. .................. 552/526; 552/648; 552/650; 540/33
(58) Field of Classification Search ............. 552/526
See application file for complete search history.

(56) References Cited

U.S. PATENT DOCUMENTS 3,927,046 A 12/1975 van den Broek

FOREIGN PATENT DOCUMENTS

EP 0114984 A2 8/1984

OTHER PUBLICATIONS

Hongwo Gao; Xiangdong Su, Liming Zhou, and Zhensu Li. Synthesis of 13–ethyl–11–methylene–18,19–dinor–17-alpha–pregn–4–en–20–yn–17–ol.Organic Preparations and Procedures International (1997), 29(5), 572–576.

Hongwo Gao, Xiangdong Su, Lei Huang, and Zhensu Li. An Improved Synthesis of 13beta–ethyl–11–methylenegon–4–en–3, 17–dione. Synthetic Communications (1997), 27(11), 1981–17.

Zhou Wei–Shan, Cai Feng, and Shen Ji–Ming, Enzymatic Hydroxlation of 18–methylgona–4–an–3–one. Huaxue Xuebao. [Acta Chimica Sinica]. April, (2001), 59(4), 604–609 (Translation).

Merck Index. 12th ed. Merck: Whitehouse Station, NJ, 2007; 2971.

Translation of EP0144984.

Basic terminology of stereochemistry. (IUPAC Recommendations 1996).

*Primary Examiner*—Gary L. Kunz

(57) ABSTRACT

The present invention relates to a new process of synthesis and to some new intermediates for the preparation of steroids with progestogen activity, more particularly, for the preparation of Desogestrel of formula (I). Said process is characterized by the regioselective reduction of the compound of formula (II) to give the intermediate of formula (III).

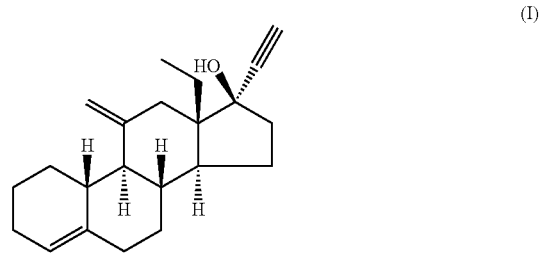

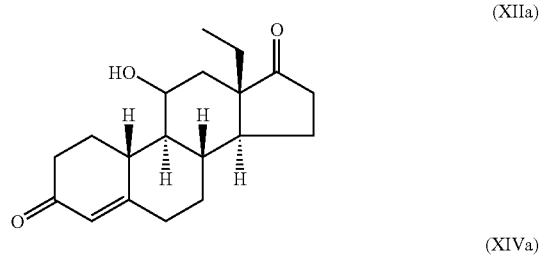

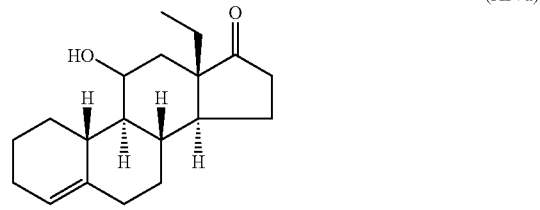

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 19 is cancelled.

New claims 31 and 32 are added and determined to be patentable.

Claims 1-18 and 20-30 were not reexamined.

*31. A method of preparing Desogestrel comprising providing two or more compounds of formula*

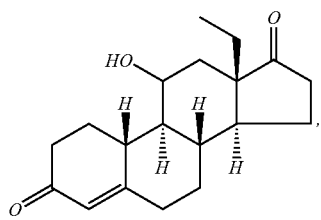

XIIa

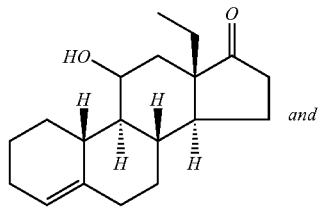

XIVa and

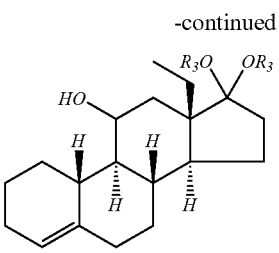

XV

*as intermediates and reacting said intermediates to produce Desogestrel, wherein $R_3$ represents a $C_1$-$C_5$ alkyl group or the $R_3$ groups together represent a -$(CH_2)_n$- chain wherein n is an integer from 2 to 4, optionally substituted by one or more methyl groups.*

*32. A method of preparing Desogestrel comprising providing one or more compounds of formula*

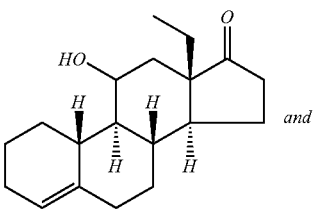

XIVa and

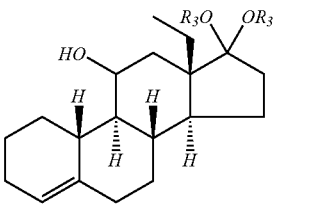

XV

*as intermediates and reacting said intermediates to produce Desogestrel, wherein $R_3$, represents a $C_1$-$C_5$ alkyl group or the $R_3$ groups together represent a -$(CH_2)n$ - chain wherein n is an integer from 2 to 4, optionally substituted by one or more methyl groups.*

\* \* \* \* \*